United States Patent [19]

Langhauser et al.

[11] Patent Number: 5,554,776
[45] Date of Patent: Sep. 10, 1996

[54] RACEMIC METALLOCENE COMPLEXES AND THEIR PREPARATION

[75] Inventors: Franz Langhauser, Bad Dürkheim; Jürgen Kerth, Carlsberg; Günther Schweier, Friedelsheim, all of Germany; Hans-Herbert Brintzinger, Taegerswilen, Switzerland; Stefan Mansel, Konstanz, Germany

[73] Assignee: BASF Aktiengesellschaft, Ludwigshafen, Germany

[21] Appl. No.: 328,777

[22] Filed: Oct. 28, 1994

[30] Foreign Application Priority Data

Oct. 30, 1993 [DE] Germany .......................... 43 37 232.5

[51] Int. Cl.$^6$ .............................. C07F 17/00; C07F 7/00; C07F 9/00
[52] U.S. Cl. ................... 556/11; 556/12; 556/28; 556/43; 556/53; 556/56; 526/126; 526/160; 526/348; 526/943; 502/152; 502/158
[58] Field of Search ................. 556/43, 53, 56, 556/28, 11, 12

[56] References Cited

FOREIGN PATENT DOCUMENTS 344887  12/1989  European Pat. Off. .
544308  6/1993   European Pat. Off. .

OTHER PUBLICATIONS

Grossman et al., *J. Am. Chem. Soc.*, vol. 113, 1991, pp. 2321–2322.
Wild et al., *J. of Org. Chem.* vol. 232, 1982, pp. 233–247.
Wiesenfeldt et al., *J. of Org. Chem.* vol. 369, 1989, pp. 359–370.

*Primary Examiner*—Porfirio Nazario-Gonzales
*Attorney, Agent, or Firm*—Keil & Weinkauf

[57] ABSTRACT

Metallocene complexes of the formula I

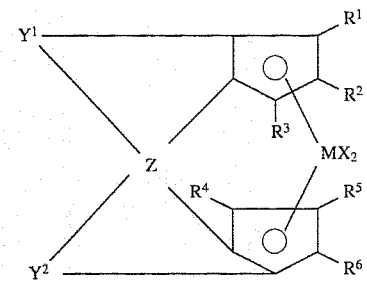

where

M is titanium, zirconium, hafnium, vanadium, niobium or tantalum,

X inter alia is fluorine, chlorine, bromine, iodine or hydrogen, $R^1$ to $R^6$ inter alia are each hydrogen or $C_1$–$C_{10}$-alkyl, Z is silicon, germanium, tin or carbon, $Y^1$ and $Y^2$ are each

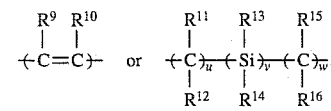

$R^9$ to $R^{16}$ inter alia are each hydrogen or $C_1$–$C_{10}$-alkyl, and u, v and w are each an integer from 0 to 7, with the proviso that the sum u+v+w is ≧2, and cyclopentadienyl compounds of the formula II

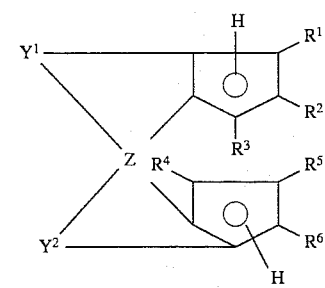

and cyclopentadienyl compound of the formula III

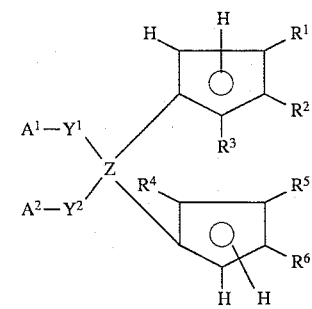

as intermediates.

3 Claims, 1 Drawing Sheet

RACEMIC METALLOCENE COMPLEXES AND THEIR PREPARATION

The present invention relates to metallocene complexes of the formula I

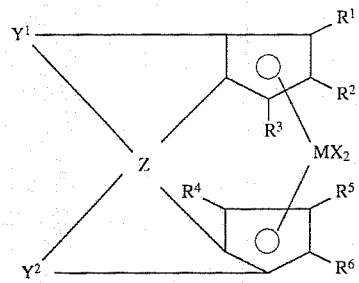

where

M is titanium, zirconium, hafnium, vanadium, niobium or tantalum,

X is fluorine, chlorine, bromine, iodine, hydrogen, $C_1$–$C_{10}$-alkyl, $C_6$–$C_{15}$-aryl or —$OR^7$, $R^7$ is $C_1$–$C_{10}$-alkyl, $C_6$–$C_{15}$-aryl, alkylaryl, aryl-alkyl, fluoroalkyl or fluoroaryl where each alkyl radical is of 1 to 10 carbon atoms and each aryl radical is from 6 to 20 carbon atoms, $R^1$ to $R^6$ are each hydrogen, $C_1$–$C_{10}$-alkyl, 5-membered to 7-membered cycloalkyl which in turn may carry $C_1$–$C_{10}$-alkyl radicals as substituents, $C_6$–$C_{15}$-aryl or arylalkyl, where two adjacent radicals together may furthermore be a cyclic group of 4 to 15, preferably 8 to 15, carbon atoms, or $Si(R^8)_3$ $R^8$ is $C_1$–$C_{10}$-alkyl, $C_6$–$C_{15}$-aryl or $C_3$–$C_{10}$-cycloalkyl, Z is silicon, germanium, tin or carbon,

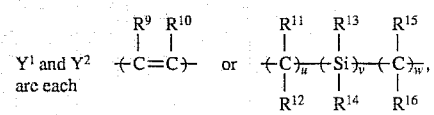

$R^9$ to $R^{16}$ are each hydrogen, $C_1$–$C_{10}$-alkyl, 5-membered to 7-membered cycloalkyl which in turn may carry $C_1$–$C_{10}$-alkyl radicals as substituents, $C_6$–$C_{15}$-aryl or arylalkyl, where two adjacent radicals together may furthermore be a cyclic group of 4 to 15 carbon atoms, or $Si(R^{17})_3$, $R^{17}$ is $C_1$–$C_{10}$-alkyl, $C_6$–$C_{15}$-aryl or $C_3$–$C_{10}$-cycloalkyl and u, v and w are each an integer from 0 to 7, with the proviso that the sum u+v+w is ≧2.

The present invention furthermore relates to cyclopentadienyl compounds of the formula II

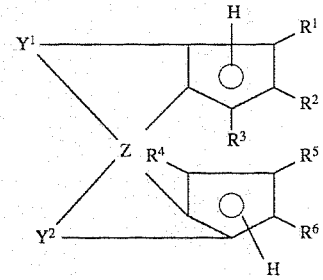

and cyclopentadienyl compounds of the formula III

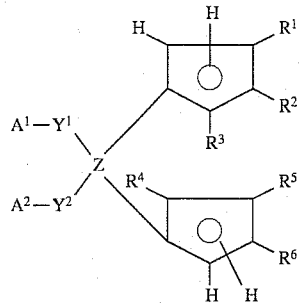

where $A^1$ and $A^2$ are each fluorine, chlorine, bromine, iodine or —$R^{18}OSO_3$, and $R^{18}$ is $C_1$–$C_{10}$-alkyl, $C_6$–$C_{15}$-aryl or $C_3$–$C_{10}$-cycloalkyl, and processes for the preparation of such metallocene complexes I, cyclopentadienyl compounds II and cyclopentadienyl compounds III and the use of the cyclopentadienyl compounds III for the preparation of cyclopentadienyl compounds II, the use of the cyclopentadienyl compounds II for the preparation of the metallocene complexes I and the use of the metallocene complexes I as catalysts for the polymerization of olefins.

For the stereoselective polymerization of prochiral olefins with metallocene catalysts, it is necessary to use chiral, stereorigid, ie. bridged, metallocene complexes. Mixtures of the racemic and meso forms, as described in H. Wiesenfeldt, A. Reinmuth, E. Barsties, K. Evertz and H.-H. Brintzinger, J. Organomet. Chem. 369 (1989), 359–370 are formed in the preparation of isospecific, bridged metallocene complexes. Particularly in the polymerization of propylene, only the racemic forms give effective catalysts for the polymerization, whereas the meso forms have comparatively little activity and give low molecular weight, atactic material, necessitating separation of the racemic and meso forms. This separation can be carried out by fractional crystallisation or extraction, as described in EP-A 344 887, or by chromatographic working-up, described in F. R. W. P. Wild, L. Zsolnai, G. Huttner and H. H. Brintzinger, J. Organomet. Chem. 232 (1982), 233–247 and R. B. Grossman, W. M. Davis and S. L. Buchwald, J. Am. Chem. Soc. 113 (1991), 2321–2322. However, the separation of the individual isomers entails considerable expense and is therefore not practicable for industrial applications.

It is an object of the present invention to provide metallocene complexes which make these working-up steps very substantially superfluous.

We have found that this object is achieved by the metallocene complexes I defined at the outset.

We have furthermore found cyclopentadienyl compounds II and cyclopentadienyl compounds III and processes for the preparation of such metallocene complexes I, cyclopentadienyl compounds II and cyclopentadienyl compounds III and the use of the cyclopentadienyl compounds III for the preparation of the cyclopentadienyl compounds II, the use of the cyclopentadienyl compounds II for the preparation of the metallocene complexes I and the use of the metallocene complexes I as catalysts for the polymerization of olefins.

Preferred novel metallocene complexes of the general formula I

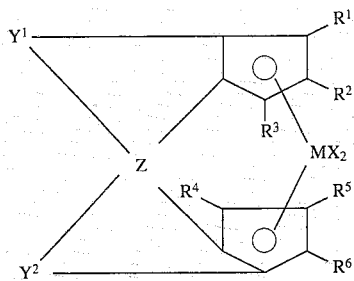

are those in which

M is zirconium or hafnium

X is chlorine or $C_1$–$C_4$-alkyl $R^1$ to $R^6$ are each hydrogen, $C_1$–$C_{10}$-alkyl or phenyl Z is silicon or carbon,

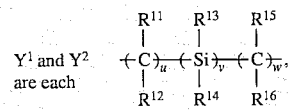

and $R^{11}$ to $R^{16}$ are each hydrogen or $C_1$–$C_4$-alkyl.

Particularly preferred metallocene complexes I are those in which the two substituted cyclopentadienyl systems are identical and $Y^1$ and $Y^2$ are identical, ie. symmetrical compounds. Particularly preferred substituents $Y^1$ and $Y^2$ are

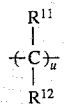

where $R^{11}$ and $R^{12}$ are each hydrogen or methyl and u is from 2 to 5, and

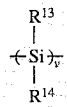

where $R^{13}$ and $R^{14}$ are each methyl and v is 2 or 3.

The following are particularly preferred: bis(spirosilacyclohexane-[b]-tert-butylcyclopentadienyl)zirconium dichloride bis(spirosilacyclohexane-[b]-methylcyclopentadienyl)zirconium dichloride bis(spirosilacyclohexane-[b]-phenylcyclopentadienyl)zirconium dichloride bis(spirosilacyclohexane-[b]-tert-butylcyclopentadienyl) hafnium dichloride bis(spirosilacyclohexane-[b]-methylcyclopentadienyl)hafnium dichloride, bis(spirosilacyclohexane-[b]-phenylcyclopentadienyl)hafnium dichloride, bis-(spirosilacyclohexane-[b]-tert-butylcyclopentadienyl) zirconiumdimethyl, bis(spirosilacyclohexane-[b]-methylcyclopentadienyl)zirconiumdimethyl and bis(spirosilacyclohexane-[b]-phenylcyclopentadienyl)zirconiumdimethyl.

The novel metallocene complexes I can be prepared in such a way that the cyclopentadienyl compounds II

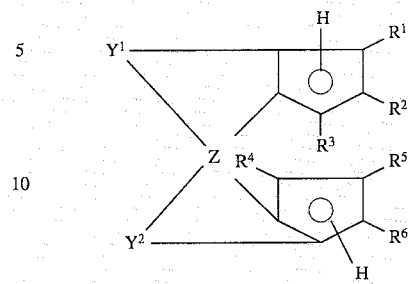

and the cyclopentadienyl compounds III

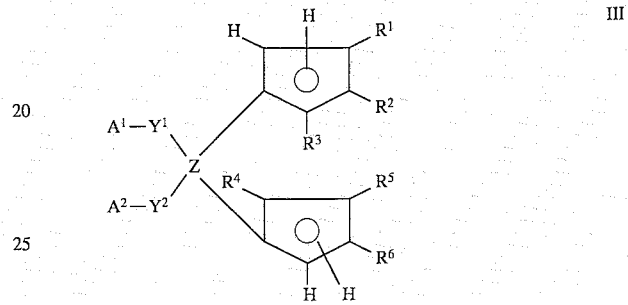

occur as intermediates. In the case of the cyclopentadienyl compounds II and the cyclopentadienyl compounds III, the statements made in connnection with the metallocene complexes I are applicable with regard to the preferred substituents. Among the radicals $A^1$ and $A^2$, chlorine and bromine are mentioned as being preferred.

A preferred process for the preparation of the metallocene complexes I and hence also for the preparation of the cyclopentadienyl compounds II and of the cyclopentadienyl compounds III is the following:

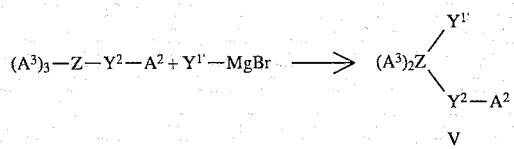

where $A^3$ is fluorine, chlorine, bromine or iodine, preferably chlorine, and $Y^{1'}$ is $Y^1$ with a terminal double bond.

This reaction is known in principle and is described, for example, in R. E. Scott and K. C. Frisch, J. Am. Chem. Soc. 73 (1951) 2599–2600.

The reaction

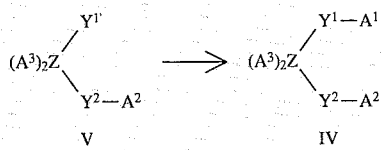

is preferably carried out by an addition reaction with H—$A^1$, in particular H—Br, as described in principle in Houben-Weyl Volume IV/5a, pages 454–456, or J. E. Francis and L. C. Leitch, Canad. J. Chem. 35 (1957), 500–503.

Reacting IV with

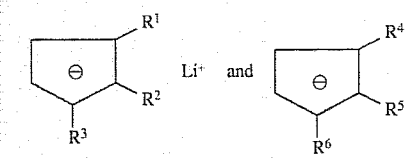

gives the cyclopentadienyl compounds III, which can be reacted with metalating agents, such as alkali metal alkyls, alkaline earth metal alkyls, alkali metal hydrides or alkaline earth metal hydrides, preferably n-butyllithium, to give the cyclopentadienyl compounds II.

The cyclopentadienyl compounds II can be converted into the novel metallocene complexes I by reaction with metalating agents, such as alkali metal alkyls or alkaline earth metal alkyls, alkali metal hydrides or alkaline earth metal hydrides, preferably n-butyllithium, and subsequent addition of $MX_4$.

The reaction conditions for the preparation of the cyclopentadienyl compounds III are not critical per se. Usually, organic solvents, such as ethers and/or hydrocarbons, preferably a mixture of tetrahydrofuran (THF) and pentane, are added to IV and the mixture is cooled to temperatures of from $-80°$ to $0°$ C. The corresponding cyclopentadienyl-lithium compounds, to which a solvent, such as THF, has preferably been added, are then introduced. After heating to room temperature, the mixture is worked up by adding an aqueous solution of ammonium salt, preferably a saturated ammonium chloride solution, and separating the phases.

The reaction conditions for the preparation of the cyclopentadienyl compounds II and of the metallocene complexes I are also not critical; the procedure is preferably similar to the method described for the preparation of the cyclopentadienyl compounds III.

This gives the metallocene complexes I which are suitable for the polymerization of olefins and are present in their racemic forms Ia and Ib

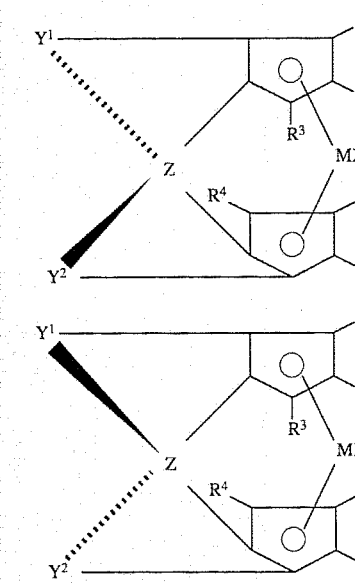

and not meso forms.

BRIEF DESCRIPTION OF THE DRAWING

The FIGURE represents the crystalline structure of compound II.

Example

Figure 1:
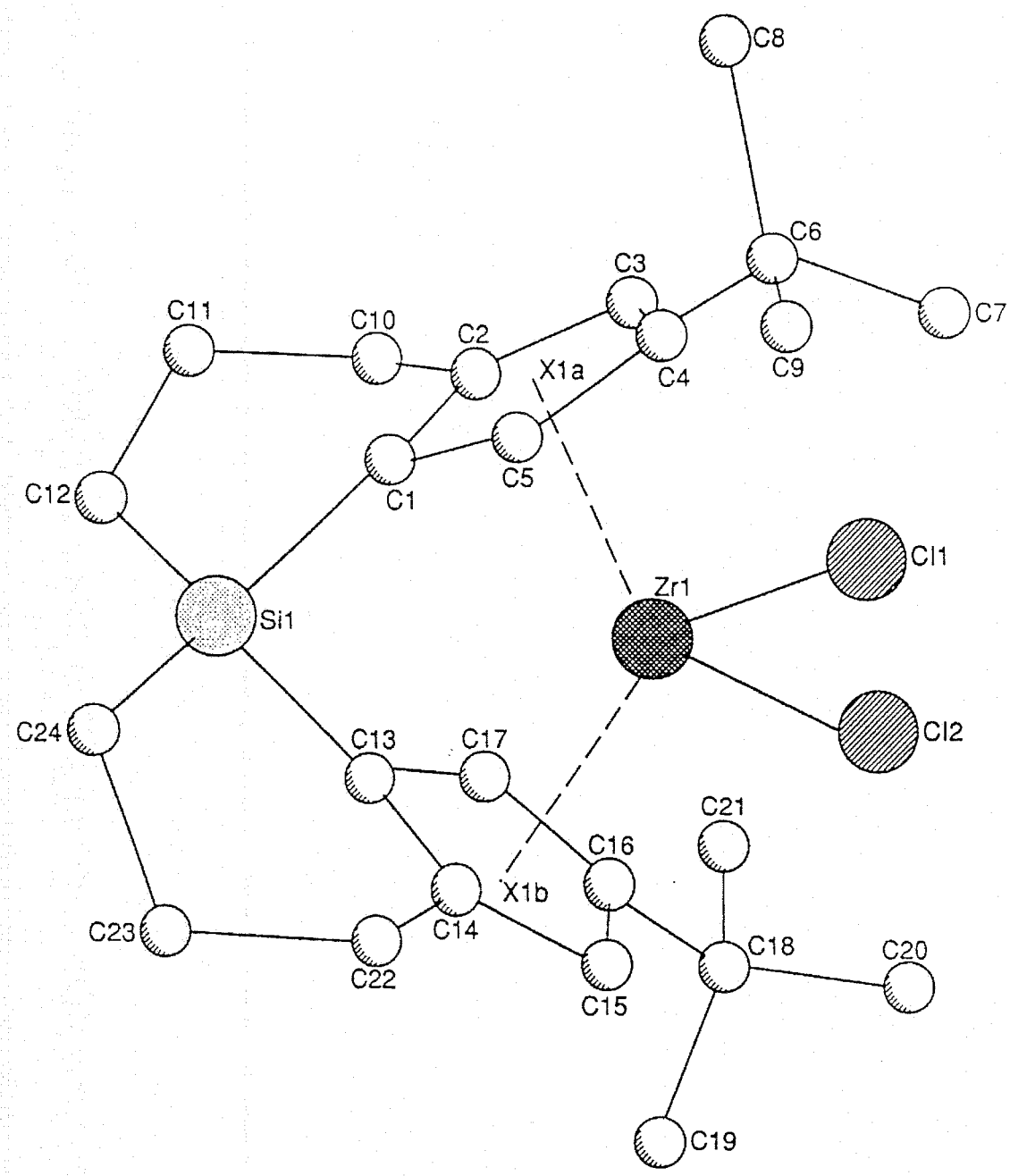

Preparation of bis(spirosilacyclohexane-[b]-tert-butylcyclopentadienyl) zirconium dichloride II 1) Preparation of 3-bromopropyl-3-chloropropyldichlorosilane IV 1

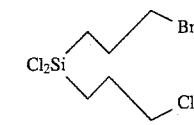

22 g (0.1 mol) of allyl-3-chloropropyldichlorosilane were initially taken in a quartz glass vessel and cooled in an ice bath. With exposure to UV light, hydrogen bromide gas was passed in through an airleak tube over a period of 2 hours. Exposure was then continued for a further hour. The subsequent distillation under reduced pressure gave, at 85° C./0.6 mmHg, 23.5 g (78% of theory) of the product IV 1 as a clear liquid.

| $^1$H-NMR (CDCl$_3$): | | | |
|---|---|---|---|
| δ [ppm] | Multiplicity | Assignment | Number |
| 3.58 | t | —C$\underline{H}_2$Cl | 2 |
| 3.45 | t | —C$\underline{H}_2$—Br | 2 |
| 2.04 | m | —CH$_2$—C$\underline{H}_2$—CH$_2$ | 4 |
| 1.28 | m | —Si—C$\underline{H}_2$ | 4 |

MS (EI/70 EV/30° C.) $C_6H_{12}BrCl_3Si$ [298.4]: 221 [M - $C_3H_6Cl$]$^+$; 177 [M-$C_3H_6Br$]$^+$; 63[$C_2H_4Cl$]$^+$; 42 [$C_3H_6$]$^+$.

2) Preparation of 3-bromopropyl-3-chloropropyl-bis(tert-butylcyclopentadienyl)silane III 1

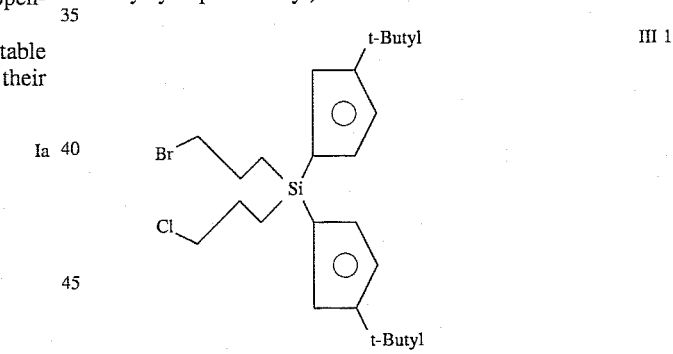

8 g (27 mmol) of IV 1 were dissolved in 50 ml of tetrahydrofuran and 70 ml of pentane and the solution was cooled in an ice bath. 6.8 g (54 mmol) of tert-butylcyclopentadienyllithium, dissolved in 30 ml of THF, were added dropwise in the course of 2 hours. After the end of the addition, the mixture was heated to room temperature and stirred for a further hour. Thereafter, 100 ml of saturated ammonium chloride solution were added and the phases were separated. The organic phase was washed with 50 ml of water and the aqueous phase with 50 ml of pentane. The combined organic phases were dried over anhydrous magnesium sulfate and filtered. After removal of the solvent, 9.5 g (75% of theory) of III 1 remained behind as a yellow oil.

| $^1$H-NMR (CDCl$_3$): | | | |
|---|---|---|---|
| δ [ppm] | Multiplicity | Assignment | Number |
| 6.67 | s | Cp (olefinic) | 2 |

-continued

<sup>1</sup>H-NMR (CDCl₃):

| δ [ppm] | Multiplicity | Assignment | Number |
|---|---|---|---|
| 6.50 | s | Cp (olefinic) | 2 |
| 6.09 | s | Cp (olefinic) | 2 |
| 3.41 | m | —CH₂—Cl | 2 |
| 3.38 | m | —CH₂—Br | 2 |
| 3.28 | m | Cp (aliphatic) | 2 |
| 1.74 | m | —CH₂—CH₂—CH₂ | 4 |
| 1.20 | s | tert-butyl | 18 |
| 0.94–0.44 | m | —Si—CH₂— | 4 |

Cp = cyclopentadienyl protons
MS (EI/70 EV/110° C.) C₂₄H₃₈BrClSi [469,7]: 470 [M]⁺; 455 [M - CH₃]⁺; 413 [M - tert-butyl]⁺; 349 [M - tert-butyl-cyclopentadienyl]⁺.

Elemental analysis: found: C 60.67; H 7.86 calculated: C 61.37; H 8.15

3) Preparation of bis(cyclohexane-[b]-tert-butylcyclopentadienyl)spirosilane II 1

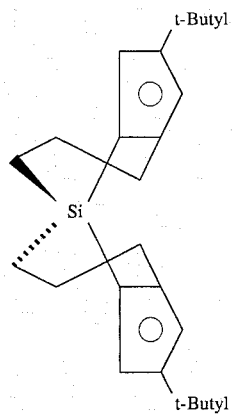

2 g (4.2 mmol) of III 1 were dissolved in 20 ml of pentane and cooled in an ice bath. 5.3 ml of n-butyllithium (1.6 molar in heptane/8.5 mmol) were added by means of a syringe. The reaction mixture was allowed to reach room temperature and was stirred for a further hour. The precipitate formed was allowed to settle out and the supernatant solution was filtered off with suction. After dissolution of the lithium salt in tetrahydrofuran, stirring was carried out for a further 40 hours at room temperature. 50 ml of saturated ammonium chloride solution and 50 ml of pentane were added, after which the phases were separated. The organic phase was washed with 50 ml of water and the aqueous phase with 50 ml of pentane. The combined organic phases were dried over magnesium sulfate and then evaporated down in a rotary evaporator. The residue was dried under reduced pressure from an oil pump. 1.45 g (77% of theory) of II 1 were obtained as a yellow oil.

| δ [ppm] | Multiplicity | Assignment | Number |
|---|---|---|---|
| 6.70–5.45 | m | Cp (olefinic) | 4 |
| 3.50–2.60 | m | Cp (olefinic) | 2 |
| 1.20 | m | tert-butyl | 18 |
| 2.60–0.05 | m | aliphatic ring proton | 12 |

MS (EI/70 EV/75° C.) C₂₄H₃₈Si [352.3]: 352 [M]⁺; 337 [M - CH₃]⁺; 295 [M - tert-butyl]⁺; 231 [M - tert-butylcyclopentadienyl]⁺.

4) Preparation of bis(spirosilacyclohexane-[b]-tert-butyl-cyclopentadienyl)zirconium dichloride I 1

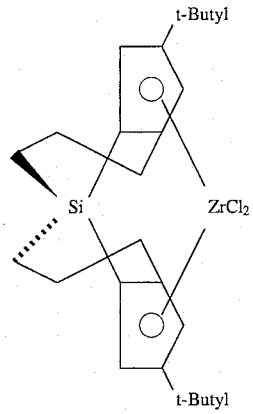

1 g (2.8 mmol) of II 1 was dissolved in 40 ml of pentane, and 3.5 ml of n-butyllithium solution (1.6 molar in hexane/5.6 mmol) were added. After 1 hour, the precipitated lithium salt was allowed to settle out and the supernatant solution was filtered off under suction. Drying under reduced pressure from an oil pump gave 1 g (2,7 mmol) of lithium salt, which was stirred with 0.7 g (3 mmol) of ZrCl₄. 30 ml of toluene were added to this solid mixture and the suspension was stirred for 20 hours at room temperature. The reaction mixture was then evaporated to dryness under reduced pressure and the residue was taken up in 50 ml of pentane. At −80° C., 20 ml (1.4% of theory) of the compound I 1 crystallized.

<sup>1</sup>H-NMR (CDCl₃):

| δ [ppm] | Multiplicity | Assignment | Number |
|---|---|---|---|
| 6.71 and 5.47 | d | Cp | 4 |
| 1.49 | s | tert-butyl | 18 |
| 1.46–0.82 | m | aliphatic ring proton | 12 |

MS (EI/70 EV/220° C.) C₂₄H₃₄Cl₂SiZr [512.3]: 512 [M]⁺; 497 [M-CH₃]⁺; 461 [M-CH₃—HCl]⁺.
(cf. FIG. 1: Crystal structure of I1)

We claim:
1. A metallocene complex of the formula I

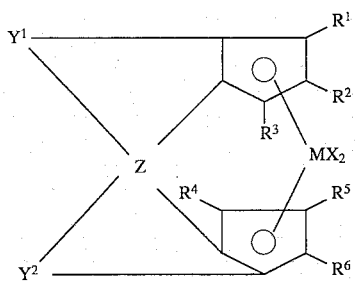

where
M is titanium, zirconium, hafnium, vanadium, niobium or tantalum,
X is fluorine, chlorine, bromine, iodine, hydrogen, $C_1$–$C_{10}$-alkyl, $C_6$–$C_{15}$-aryl or —OR$^7$,
R$^7$ is $C_1$–$C_{10}$-alkyl, $C_6$–$C_{15}$-aryl, alkylaryl, aryl-alkyl, fluoroalkyl or fluoroaryl where each alkyl radical is of 1 to 10 carbon atoms and each aryl radical is from 6 to 20 carbon atoms,
R$^1$ to R$^6$ are each hydrogen, $C_1$–$C_{10}$-alkyl, 5-membered to 7-membered cycloalkyl which in turn may carry $C_1$–$C_{10}$-alkyl radicals as substituents, $C_6$–$C_{15}$-aryl or arylalkyl, where two adjacent radicals together may furthermore be a cyclic group of 4 to 15 carbon atoms, or $Si(R^8)_3$ $R^8$ is $C_1$–$C_{10}$-alkyl, $C_6$–$C_{15}$-aryl or $C_3$–$C_{10}$-cycloalkyl, Z is silicon, germanium, tin or carbon, $Y^1$ and $Y^2$ are each 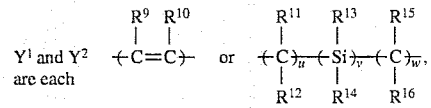

$R^9$ to $R^{16}$ are each hydrogen, $C_1$–$C_{10}$-alkyl, 5-membered to 7-membered cycloalkyl which in turn may carry $C_1$–$C_{10}$-alkyl radicals as substituents, $C_6$–$C_{15}$-aryl or arylalkyl, where two adjacent radicals together may furthermore be a cyclic group of 4 to 15 carbon atoms, or $Si(R^{17})_3$ $R^{17}$ is $C_1$–$C_{10}$-alkyl, $C_6$–$C_{15}$-aryl or $C_3$–$C_{10}$-cycloalkyl and u, v and w are each an integer from 0 to 7, with the proviso that the sum u+v+w is $\geq 2$.

2. The metallocene complex of the formula I of claim 1 which is bis(spirosilacyclohexane-[b]-tert-butylcyclopentadienyl)zirconium dichloride.

3. A process for the preparation of the metallocene complex I of claim 1, wherein a cyclopentadienyl compound of the formula II

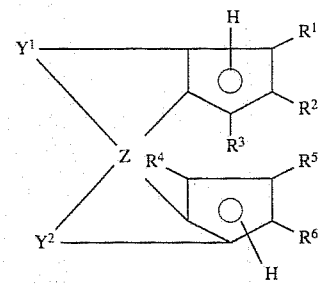

$R^1$ to $R^6$ are each hydrogen, $C_1$–$C_{10}$-alkyl, 5-membered to 7-membered cycloalkyl which in turn may carry $C_1$–$C_{10}$-alkyl radicals as substituents, $C_6$–$C_{15}$-aryl or arylalkyl, where two adjacent radicals together may furthermore be a cyclic group of 4 to 15 carbon atoms, or $Si(R^8)_3$ $R^8$ is $C_1$–$C_{10}$-alkyl, $C_6$–$C_{15}$-aryl or $C_3$–$C_{10}$-cycloalkyl, Z is silicon, germanium, tin or carbon, $Y^1$ and $Y^2$ are each 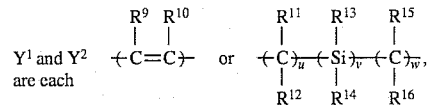

$R^9$ to $R^{16}$ are each hydrogen, $C_1$–$C_{10}$-alkyl, 5-membered to 7-membered cycloalkyl which in turn may carry $C_1$–$C_{10}$-alkyl radicals as substituents, $C_6$–$C_{15}$-aryl or arylalkyl, where two adjacent radicals together may furthermore be a cyclic group of 4 to 15 carbon atoms, or $Si(R^{17})_3$ $R^{17}$ is $C_1$–$C_{10}$-alkyl, $C_6$–$C_{15}$-aryl or $C_3$–$C_{10}$-cycloalkyl and u, v and w are each an integer from 0 to 7, with the proviso that the sum u+v+w is $\geq 2$ is reacted with a metalating agent and $MX_4$ is then added wherein M is titanium, zirconium, hafnium, vanadium, niobium or tantalum, X is fluorine, chlorine, bromine, iodine, hydrogen, $C_1$–$C_{10}$-alkyl, $C_6$–$C_{15}$-aryl or —$OR^7$ and $R^7$ is $C_1$–$C_{10}$-alkyl, $C_6$–$C_{15}$-aryl, alkylaryl, arylalkyl, fluoroalkyl, or fluoroaryl where each alkyl radical is of 1 to 10 carbon atoms and each aryl radical is from 6 to 20 carbon atoms.

\* \* \* \* \*